(12) United States Patent
Chang et al.

(10) Patent No.: US 12,144,488 B2
(45) Date of Patent: Nov. 19, 2024

(54) MAGNETICALLY CONTROLLED POWER BUTTON AND GYROSCOPE EXTERNAL TO THE LUNG USED TO MEASURE ORIENTATION OF INSTRUMENT IN THE LUNG

(71) Applicant: Covidien LP, Mansfield, MA (US)

(72) Inventors: Allison T. Chang, Minneapolis, MN (US); Kurt L Moberg, Ramsey, MN (US); Raelyn E. Nyren, Ham Lake, MN (US); Keith Jasperson, Andover, MN (US)

(73) Assignee: Covidien LP, Mansfield, MA (US)

( * ) Notice: Subject to any disclaimer, the term of this patent is extended or adjusted under 35 U.S.C. 154(b) by 290 days.

(21) Appl. No.: 17/573,499

(22) Filed: Jan. 11, 2022

(65) Prior Publication Data

US 2022/0218184 A1 Jul. 14, 2022

Related U.S. Application Data

(60) Provisional application No. 63/137,483, filed on Jan. 14, 2021.

(51) Int. Cl.
*A61B 1/00* (2006.01)
*A61B 1/267* (2006.01)
*A61B 5/00* (2006.01)
*A61B 5/06* (2006.01)

(52) U.S. Cl.
CPC ...... *A61B 1/00158* (2013.01); *A61B 1/00016* (2013.01); *A61B 1/2676* (2013.01); *A61B 5/0022* (2013.01); *A61B 5/062* (2013.01); *A61B 5/6852* (2013.01); *A61B 2562/0219* (2013.01)

(58) Field of Classification Search
CPC ............... A61B 1/00158; A61B 5/062; A61B 2562/0219; A61B 5/6852; A61B 1/2676; A61B 5/08; A61B 1/00016; A61B 5/0022; A61B 5/0002
See application file for complete search history.

(56) References Cited

U.S. PATENT DOCUMENTS

| | | | |
|---|---|---|---|
| 8,152,715 B2 * | 4/2012 | Root | A61B 1/0669 600/178 |
| 9,496,927 B1 | 11/2016 | Grinberg et al. | |
| 2004/0249267 A1 * | 12/2004 | Gilboa | A61B 1/00154 600/424 |
| 2008/0071170 A1 * | 3/2008 | Kenneth | A61B 1/01 600/431 |
| 2010/0277304 A1 | 11/2010 | Haartsen | |
| 2011/0070826 A1 | 3/2011 | Griffin et al. | |

(Continued)

OTHER PUBLICATIONS

D. Arenberg, "Electromagnetic navigation guided bronchoscopy", Cancer Imaging, vol. 9, pp. 89-95, Oct. 2009 (Year: 2009).*

(Continued)

*Primary Examiner* — Joel Lamprecht
*Assistant Examiner* — Nyrobi Celestine
(74) *Attorney, Agent, or Firm* — Weber Rosselli & Cannon LLP

(57) ABSTRACT

A luminal navigation system including a catheter including a sensor and a pod including a wireless communication device, the wireless communication device transmitting data received from the sensor.

19 Claims, 19 Drawing Sheets

(56) References Cited

U.S. PATENT DOCUMENTS

| | | | |
|---|---|---|---|
| 2012/0226148 A1* | 9/2012 | Jaggi | A61B 5/06 600/424 |
| 2014/0206953 A1* | 7/2014 | Valdastri | A61B 5/0031 600/301 |
| 2014/0342671 A1 | 11/2014 | Kim et al. | |
| 2015/0164313 A1* | 6/2015 | Ouyang | A61B 1/00071 600/103 |
| 2015/0327791 A1* | 11/2015 | Greenburg | A61B 34/20 600/424 |
| 2015/0370346 A1 | 12/2015 | Smus et al. | |
| 2016/0051221 A1* | 2/2016 | Dickhans | A61B 8/0841 600/424 |
| 2017/0259037 A1* | 9/2017 | Kern | A61M 25/0067 |
| 2017/0333000 A1* | 11/2017 | Nystrom | A61B 8/445 |
| 2018/0140359 A1* | 5/2018 | Koyrakh | A61B 34/20 |
| 2018/0310995 A1* | 11/2018 | Gliner | A61B 18/148 |
| 2019/0269335 A1* | 9/2019 | Groenland | A61B 5/686 |
| 2020/0146757 A1* | 5/2020 | Fenech | A61B 34/10 |
| 2020/0188635 A1* | 6/2020 | Barrish | A61B 34/20 |
| 2020/0275860 A1* | 9/2020 | Duindam | A61B 5/062 |
| 2021/0030480 A1* | 2/2021 | McMichael | A61B 5/065 |
| 2021/0196394 A1* | 7/2021 | Govari | A61M 25/0662 |
| 2021/0369366 A1* | 12/2021 | Hwang | A61B 34/74 |
| 2022/0175468 A1* | 6/2022 | Barak | A61B 34/20 |
| 2022/0331558 A1* | 10/2022 | Averbuch | A61M 25/0136 |
| 2023/0072879 A1* | 3/2023 | Slawinski | A61B 1/2676 |

OTHER PUBLICATIONS

S. Leong et al, "Electromagnetic navigation bronchoscopy: A descriptive analysis", Journal of Thoracic Disease, vol. 4, No. 2, pp. 173-185, Mar. 2012 (Year: 2012).*

O. Rickman, "Electromagnetic Navigation-Assisted Bronchoscopy", Operative Techniques in Thoracic and Cardiovascular Surgery, vol. 19, No. 2, pp. 199-218, 2014 (Year: 2014).*

* cited by examiner

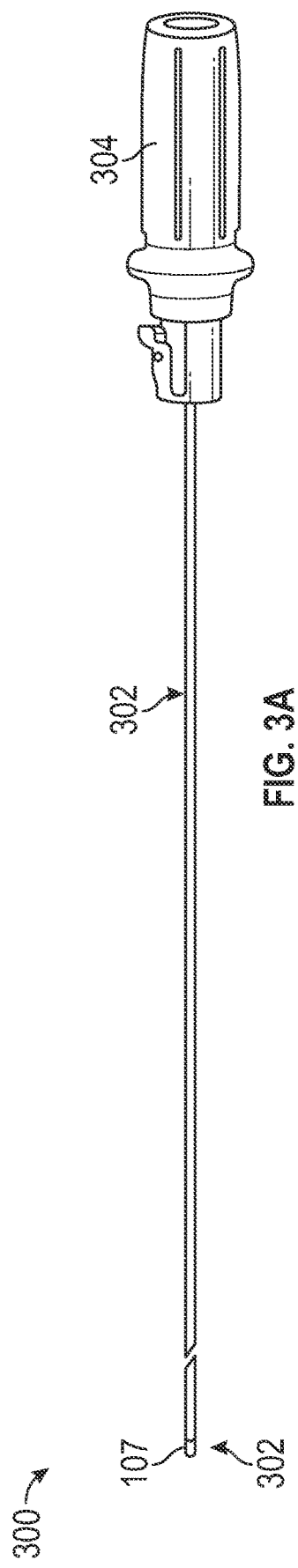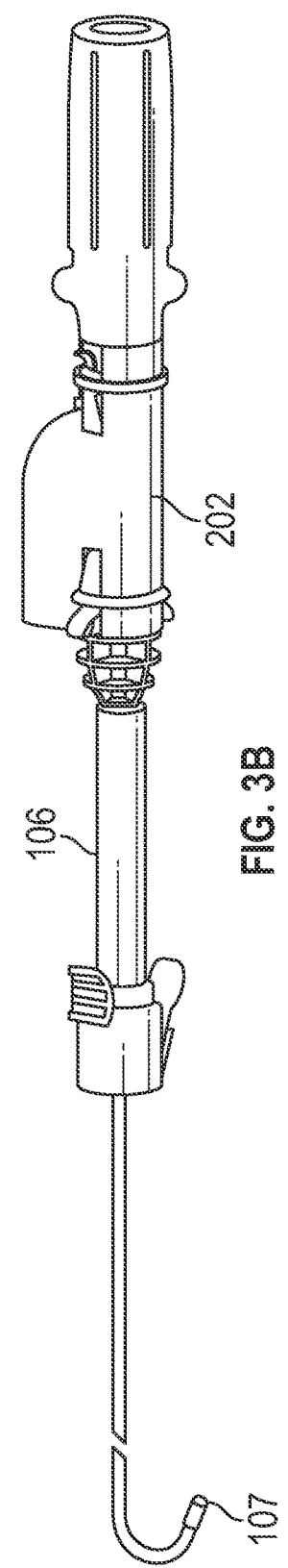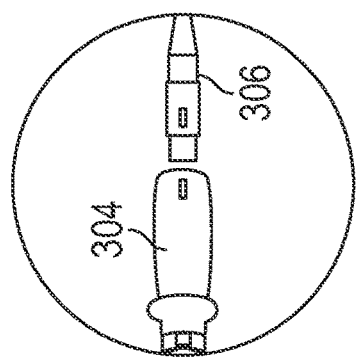
FIG. 3A
FIG. 3B
FIG. 3C

MAGNETICALLY CONTROLLED POWER BUTTON AND GYROSCOPE EXTERNAL TO THE LUNG USED TO MEASURE ORIENTATION OF INSTRUMENT IN THE LUNG

CROSS-REFERENCE TO RELATED APPLICATION

This application claims the benefit of, and priority to, U.S. Provisional Patent Application Ser. No. 63/137,483, filed on Jan. 14, 2021, the entire content of which is hereby incorporated by reference herein.

INTRODUCTION

This disclosure relates to surgical systems, and more particularly, to systems for intraluminal navigation such as navigation within the lungs.

BACKGROUND

There are several commonly applied medical methods, such as endoscopic procedures or minimally invasive procedures, for treating various maladies affecting organs including the liver, brain, heart, lungs, gall bladder, kidneys, and bones. Often, one or more imaging modalities, such as magnetic resonance imaging (MRI), ultrasound imaging, computed tomography (CT), or fluoroscopy are employed by clinicians to identify and navigate to areas of interest within a patient and ultimately a target for biopsy or treatment. In some procedures, pre-operative scans may be utilized for target identification and intraoperative guidance. However, real-time imaging may be required to obtain a more accurate and current image of the target area. Furthermore, real-time image data displaying the current location of a medical device with respect to the target and its surroundings may be needed to navigate the medical device to the target in a safe and accurate manner (e.g., without causing damage to other organs or tissue).

For example, an endoscopic approach has proven useful in navigating to areas of interest within a patient, and particularly so for areas within luminal networks of the body such as the lungs. To enable the endoscopic approach, and more particularly the bronchoscopic approach in the lungs, endobronchial navigation systems have been developed that use previously acquired MRI data or CT image data to generate a three-dimensional (3D) rendering, model, or volume of the particular body part such as the lungs.

The resulting volume generated from the MRI scan or CT scan is then utilized to create a navigation plan to facilitate the advancement of a navigation catheter (or other suitable medical device) through a bronchoscope and a branch of the bronchus of a patient to an area of interest. A locating or tracking system, such as an electromagnetic (EM) tracking system, may be utilized in conjunction with, for example, CT data, to facilitate guidance of the navigation catheter through the branch of the bronchus to the area of interest. In certain instances, the navigation catheter may be positioned within one of the airways of the branched luminal networks adjacent to, or within, the area of interest to provide access for one or more medical instruments.

Despite the successes of these systems, improvements are always desired to promote the efficient use of these systems and overcome challenges in use of these systems.

SUMMARY

One aspect of the disclosure is directed to a luminal navigation system including: a catheter configured for insertion into a bronchoscope, the catheter including a five degree of freedom (5DOF) sensor at a distal portion of the catheter. The luminal navigation system also includes a locating module configured to receive signals from the 5DOF sensor to determine an X, Y, Z location and pitch and yaw orientation of the distal portion of the catheter. The luminal navigation system also includes a pod, configured to be received between a telescoping portion of the catheter and a hub of the catheter, the pod including a wireless communication device. The luminal navigation system also includes a gyroscopic sensor located in the pod, where the gyroscopic sensor determines an amount of roll experienced by the pod, where the pod is configured to receive signals from the 5DOF sensor and the gyroscopic sensor and to transmit to the locating module the received signals and the locating module can determine the position and orientation of the distal portion of the catheter in six degrees of freedom (6DOF). Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The luminal navigation system further including a locatable guide configured for insertion into a lumen of the catheter, the locatable guide including a 6DOF sensor at a distal end and a handle on a proximal end, where signals generated by the 6DOF sensor are transmitted to the locating module. The luminal navigation system where the 6DOF sensor and the 5DOF sensor are electromagnetic sensors configured to detected magnetic fields generated by a magnetic field generator. The luminal navigation system where the pod includes an EM field detector, wherein the pod fully powers on upon detection of a magnetic field. The luminal navigation system where the pod further includes a rechargeable battery. The luminal navigation system further including a charger configured to receive the pod and to charge the rechargeable battery. The luminal navigation system where the charger is configured for wireless charging of the rechargeable battery in the pod.

Another aspect of the disclosure is directed to a luminal navigation system including: a catheter configured for insertion into a bronchoscope, the catheter including a five degree of freedom (DOF) sensor at a distal portion of the catheter. The luminal navigation system also includes a locating module configured to receive signals from the 5DOF sensor to determine an X, Y, Z location and pitch and yaw orientation of the distal portion of the catheter. The luminal navigation system also includes a locatable guide configured for insertion into a lumen of the catheter, the locatable guide including a 6DOF sensor at a distal end and a handle on a proximal end, where signals generated by the 6DOF sensor are transmitted to the locating module. The luminal navigation system also includes a pod, configured to be received between a telescoping portion of the catheter and a hub of the catheter, the pod including a wireless communication device; where the locating module receives the output from the 6DOF sensor via a cable while the locatable guide is secured in the catheter and from the 5DOF sensor via the wireless communication device following removal of the locatable guide from the catheter. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The luminal navigation system further including a gyroscopic sensor located in the pod, where the gyroscopic sensor determines an amount of roll experienced by the pod. The luminal navigation system where the pod is configured to receive signals from the 5DOF sensor and the gyroscopic sensor and to transmit to the locating module the received signals and the locating module can determine the position and orientation of the distal portion of the catheter in six degrees of freedom (6DOF). The luminal navigation system wherein the pod includes an EM field detector, wherein the pod fully powers on upon detection of a magnetic field. The luminal navigation system where the 6DOF sensor and the 5DOF sensor are electromagnetic sensors configured to detected magnetic fields generated by a magnetic field generator. The luminal navigation system where the pod further includes a rechargeable battery. The luminal navigation system further including a charger configured to receive the pod and to charge the rechargeable battery. The luminal navigation system where the charger is configured for wireless charging of the rechargeable battery in the pod. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

A further aspect of the disclosure is directed to a wireless transmitter pod for a luminal navigation catheter, including: a housing configured to mate with a catheter, the catheter including a five degrees of freedom (5DOF) sensor formed on a distal end. The wireless transmitter pod also includes a rechargeable battery secured within the housing. The wireless transmitter pod also includes a wireless communication device secured within the housing. The wireless transmitter pod also includes a gyroscopic sensor secured within the housing. The wireless transmitter pod also includes a microcontroller configured to receive signals from the 5DOF sensor and the gyroscopic sensor and to output via the wireless communication device a signal from which a position and orientation of distal portion of the catheter in six degrees of freedom (6DOF). Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The wireless transmitter pod further including at least one light-emitting diode configured to indicate a status of the rechargeable battery. The wireless transmitter pod further including at least one light emitting diode configured to indicate a connection status of the wireless communication device. The wireless transmitter pod further configured to receive a hub of the catheter, where the hub enables electrical connectivity of the sensor to the microcontroller. The wireless transmitter pod where the sensor is an electromagnetic sensor. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

BRIEF DESCRIPTION OF THE DRAWINGS

Various aspects and features of the disclosure are described hereinbelow with references to the drawings, wherein:

FIG. 3A is a profile view of a locatable guide in accordance with the disclosure;

FIG. 3B is a profile view of the locatable guide of FIG. 3A inserted into the catheter of FIG. 2A;

FIG. 3C is a profile view of a portion of FIG. 3A showing the insertion of a cable;

DETAILED DESCRIPTION

This disclosure is directed to improvements to electromagnetic (EM) navigation systems such as the ILLUMISITE system sold by MEDTRONIC PLC. In one aspect the disclosure is directed to a system enabling wireless (e.g., BLUETOOTH, or others) communication between a catheter or extended working channel (EWC) and navigation software components of the EM navigation system. Such wireless communication helps eliminate wire entanglement issues that can present themselves in currently available systems. A further aspect of the disclosure is directed to a system and method that can determine in six degrees of freedom (6DOF), X, Y, Z, pitch, yaw, and roll, the position and orientation of the distal end of the catheter or EWC within the patient. In particular, the disclosure is directed to determining the amount of roll experienced at the distal end of the catheter utilizing a gyroscopic sensor located on a proximal end of the catheter. This data can be combined with a 5DOF EM sensor located on the distal end of the catheter to provide accurate position and orientation data of the distal portion of the catheter.

Figure 1:
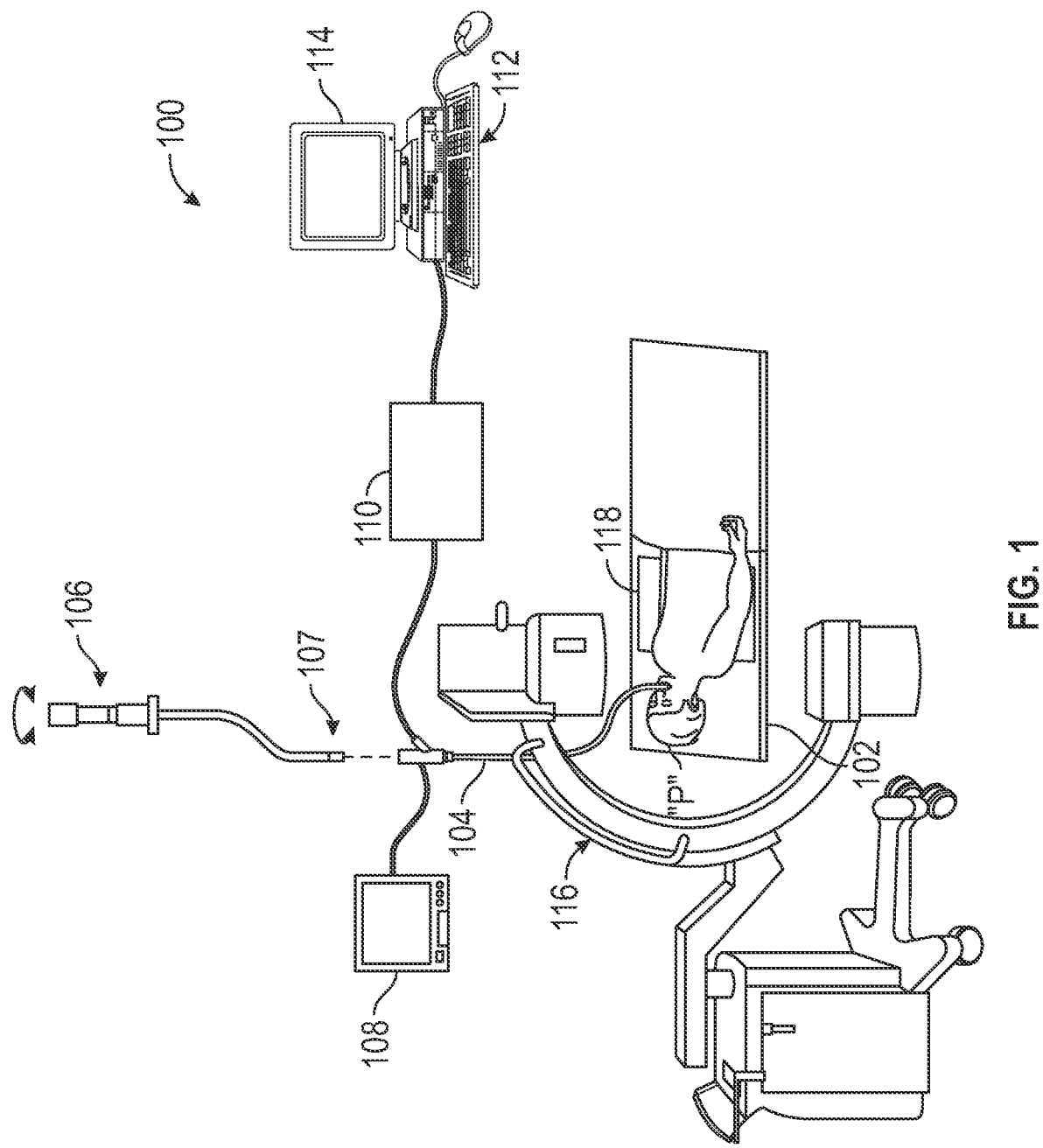
FIG. 1 is a schematic illustration of a system in accordance with the disclosure.

FIG. 1 is a perspective view of an exemplary system 100 in accordance with the disclosure. System 100 includes a table 102 on which a patient P is placed. A bronchoscope 104 is inserted into an opening in the patient. The opening could be a natural opening such as the mouth, nose, or anus. Alternatively, the opening may be formed in the patient, for example a surgical port or a simple incision. The bronchoscope 104 may include one or more optical sensors for capturing live images and video as the bronchoscope 104 is navigated into the patient P. A catheter 106 may be inserted into the bronchoscope 104 for navigating to portions of the anatomy into which the bronchoscope 104 cannot pass. A variety of tools (not shown) such as a biopsy needle, ablation needle, clamp, forceps, or others may be inserted into the catheter 106 to achieve a desired therapeutic or diagnostic purpose. One or more sensors 107 may be located at a distal end of the catheter 106. A monitor 108 may be employed to display images captured by the optical sensor on the bronchoscope 104 as it is navigated within the patient P.

The system 100 includes a locating module 110 which receives signals from catheter 106 and sensors 107 and processes the signals to generate useable data, as described in greater detail below. A computer 112, including a display 114 receives the useable data from the locating module 110, and incorporates the data into one or more applications running on the computer 112 to generate one or more user-interfaces that are presented on the display 114. Both the locating module 110 and the monitor 108 may be incorporated into or replaced by applications running on the computer 112 and images presented via a user interface on the display 114. Also depicted in FIG. 1 is a fluoroscope 116 which may be employed to construct fluoroscopic based three-dimensional volumetric data of a target area from 2D fluoroscopic images and other imaging techniques. As will be appreciated the computer 112 incudes a computer readable recording medium such as a memory for storing image data and applications that can be executed by a processor in accordance with the disclosure to perform some or all of the steps of the methods described herein.

There are known in the art a variety of pathway planning applications for pre-operatively planning a path through a luminal network such as the lungs or the vascular system. Typically, a pre-operative image data set such as one acquired from a CT scan or an MM scan is presented to a user. The target identification may be automatic, semi-automatic, or manual, and allows for determining a pathway through patient P's airways to tissue located at and around the target. In one variation the user scrolls through the image data set, which is presented as a series of slices of the 3D image data set output from the CT scan. By scrolling through the images, the user manually identifies targets within the image data set. The slices of the 3D image data set are often presented along the three axes of the patient (e.g., axial, sagittal, and coronal) allowing for simultaneous viewing of the same portion of the 3D image data set in three separate 2D images.

Additionally, the 3D image data set (e.g., acquired from the CT scan) may be processed and assembled into a three-dimensional CT volume, which is then utilized to generate a 3D model of patient P's airways by various segmentation and other image processing techniques. Both the 2D slices images and the 3D model may be displayed on a display 114 associated with computer 112. Using computer 112, various views of the 3D or enhanced 2D images may be generated and presented. The enhanced two-dimensional images may possess some three-dimensional capabilities because they are generated from the 3D image data set. The 3D model may be presented to the user from an external perspective view, an internal "fly-through" view, or other views. After identification of a target, the application may automatically generate a pathway to the target. In the example of lung navigation, the pathway may extend from the target to the trachea, for example. The application may either automatically identify the nearest airway to the target and generate the pathway, or the application may request the user identify the nearest or desired proximal airway in which to start the pathway generation to the trachea. Once selected, the pathway plan, three-dimensional model, and 3D image data set and any images derived therefrom, can be saved into memory on the computer 112 and made available for use during a procedure, which may occur immediately following the planning or at a later date.

Following, the planning phase, where targets are identified and pathways to those targets are created, a navigation phase can be commenced. With respect to the navigation phase, the locating module 110 is employed to detect the position and orientation of a distal portion of the catheter 106. The locating module 110 may utilize a transmitter mat 118 to generate an electromagnetic field in which the position of sensors 107 are placed. The sensors 107 generate a current when placed in the electromagnetic field is received by the locating module 110 and either five or six degrees of freedom (DOF) of the position of the sensor 107 and catheter 106 is determined. To accurately reflect the detected position of the catheter 106 in the pre-procedure image data set (e.g., CT or MRI images) or 3D models generated therefrom, a registration process must be undertaken.

Registration of the patient P's location on the transmitter mat 118 may be performed by moving sensor 107 through the airways of the patient P. More specifically, data pertaining to locations of sensor 107, while catheter 106 is moving through the airways, is recorded using transmitter mat 118 and locating module 110. A shape resulting from this location data is compared to an interior geometry of passages of the three-dimensional model generated in the planning phase, and a location correlation between the shape and the three-dimensional model based on the comparison is determined, e.g., utilizing the software on computer 112. In addition, the software identifies non-tissue space (e.g., air filled cavities) in the three-dimensional model. The software aligns, or registers, an image representing a location of sensor 107 with the three-dimensional model and/or two-dimensional images generated from the three-dimension model, which are based on the recorded location data and an assumption that sensor 107 locatable guide 110 remains located in non-tissue space in patient P's airways.

Though described herein with respect to EMN systems using EM sensor sensors 107 are not so limited, and the sensors may be one or more of an inertial measurement unit, shape sensor, optical sensor, ultrasound sensor, and others.

Additionally, the methods described herein may be used in conjunction with robotic systems such that robotic actuators (not shown) drive the catheter 106 proximate the target.

Figure 2A:
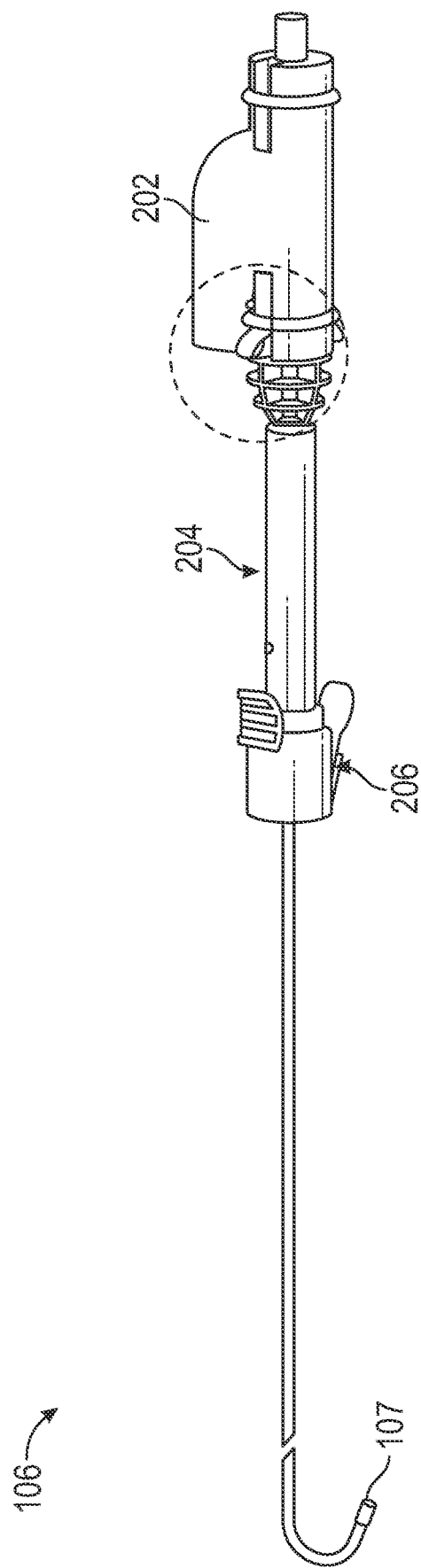
FIG. 2A is a profile view of a catheter in accordance with the disclosure.
Figure 2B:
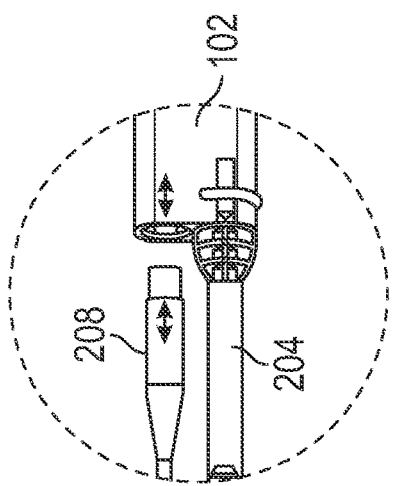
FIG. 2B is a detailed view of a portion of FIG. 2A showing the insertion of a cable.

FIG. 2A depicts a detailed view of the catheter 106, with sensor 107 located at the distal end. On a proximal end of the catheter 106, a hub 202 connects to the a telescopic portion 204 having a telescope hub 206 for connection to a bronchoscope adapter (not shown) such that the catheter 106 can be inserted into the working channel of a bronchoscope 104. The hub 202 is electrically connected to the sensor 107. As shown in FIG. 2B, a cable 208 is inserted into the hub 202 to connect the hub 202 and therewith the sensor 107 to the locating module 110 and the computer 112 via a wired connection. As described, above, the data output by the sensor 107 is used to determine the position and orientation of the catheter 106 in the patient.

FIG. 3A depicts a locatable guide 300. The locatable guide 300 is a sensor catheter that includes a sensor 107 at the distal end 302 and a handle 304 at the proximal end. The locatable guide 300 is configured for insertion into the catheter 106, as depicted in FIG. 3B. The handle 304 is in electrical communication with the sensor 107. FIG. 3C depicts the insertion of a cable 306 into the handle 304 to therewith electrically connect the sensor 107 with the locating module 110 and the computer 112 via a wired connection.

In practice, while navigating the catheter 106 to a target in the lung, following the navigation pathway, the data from the sensor 107 in the locatable guide 300 is employed for detecting location and orientation of the locatable guide 300, and therewith the distal portion of the catheter 106. The sensor 107 in the locatable guide 300 is a 6DOF sensor and provides X, Y, Z coordinates as well as pitch, yaw, and roll orientations of the sensor 107 and therewith the position and orientation of the locatable guide 300 within the EM field generated by the transmitter mat 118.

Upon reaching a desired position opposite a target, the locatable guide 300 is removed from the catheter 106 so that the lumen in the catheter is freed for insertion of other tools such as biopsy or therapeutic tools such as microwave ablation catheters, and others. With removal of the locatable guide 300 sensor data from the sensor 107 in the catheter 106 is now employed to detect the position of the catheter 106. It will be appreciated that with the removal of the locatable guide 300 and insertion of other tools the position of the distal portion of the catheter 106 may move and its position must be updated in the display 114 of the navigation view to accurately show the position of the catheter 106 in the 3D models and therewith in the patient. However, the sensor 107 in the catheter 106 is a 5DOF sensor and outputs only X, Y, Z, coordinates and pitch and yaw orientation data. Utilizing current EM sensor technology, and because of the need to maintain the lumen opening through the catheter 106, the sensor 107 in the catheter 106 does not provide an output that can be used to determine the roll orientation of the distal portion of the catheter 106.

Though described above as using the sensor 107 in the LG 300 to perform the navigation of the catheter 106 to the target following the pathway plan, the disclosure is not so limited. In some embodiments the sensor 107 in the catheter 106 may be employed for this navigation.

Another challenge of this arrangement is the use of cables 208 and 306. As can be imagined manipulating the catheter 106 through the luminal network of a patient requires repeated steps of rotation and advancement. With cable 306 extending from the handle 304 and cable 208 extending from hub 202, but both leading to the locating system 110 or to computer 112, the cables are likely to become intertwined and entangled with one another. This entanglement results in challenges when the locatable guide 300 must be removed from the catheter 106.

Figure 4:
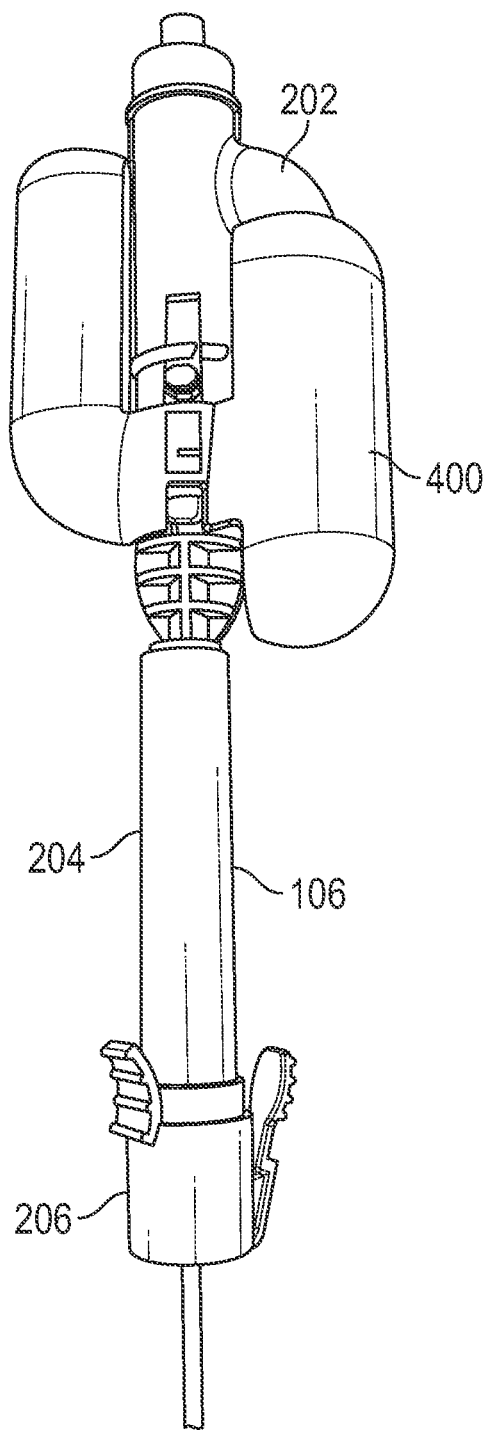
FIG. 4 is a perspective view of a wireless transmission pod incorporated as part of the catheter of FIG. 2A.

To alleviate the entangling issue, one aspect of the disclosure is directed to a wireless communication pod 400 as depicted in FIG. 4. The pod 400 is configured to mount between the hub 202 of the catheter 106, and the telescopic portion. The pod 400 may be formed of a translucent material and include one or more light emitting diodes 402 (LED). The LEDs can provide indicators that the pod 400 is properly mated to the hub 202 and capable of receiving signals from the sensor 107 at the distal end of the catheter 106 when placed in an EM field. A rechargeable battery 404 is housed within the pod 400. Those of skill in the art will recognize that a non-rechargeable battery may also be employed without departing from the scope of the disclosure. The rechargeable battery 404 is electrically connected to one or more circuit boards (not shown). The circuit boards include a BLUETOOTH transmitter or transmitter-receiver 406 capable of bidirectional or unidirectional communication with the locating module 110 and computer 112. One or more microcontrollers 407 may be employed to provide logical functions for the transmitter 406, or to translate the signals derived from the sensor 107 to configure them for transmission via the transmitter 406. The pod 400 may further include a display 408 (e.g., a liquid crystal display or an LED indicator) indicating the battery level and other information such as connection to the sensor 107, and to the computer 112. The pod 400 is intended to be re-useable, however, disposable versions are also possible.

Figure 6A:
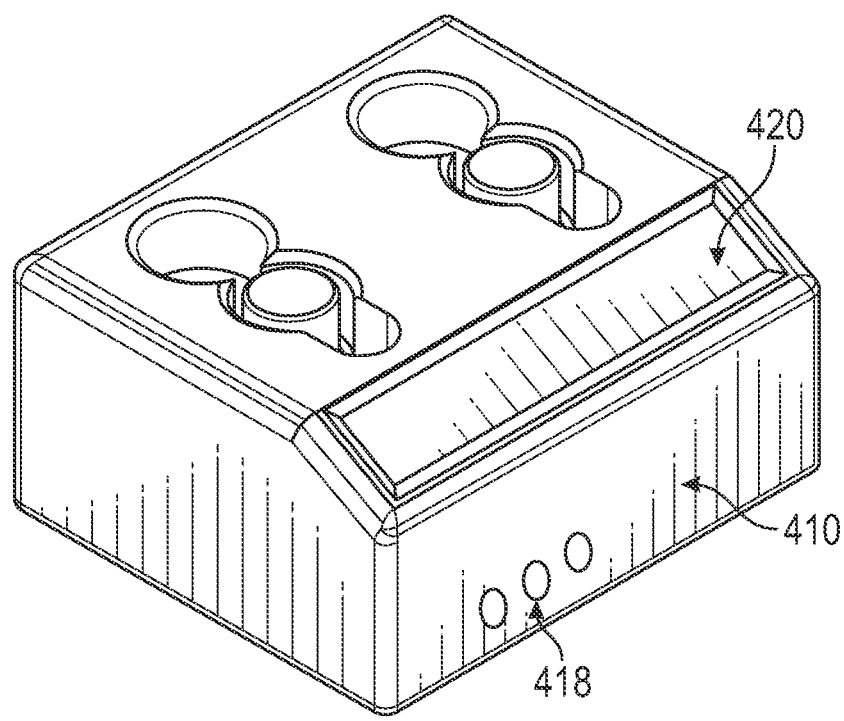
FIG. 6A is a top perspective view of a charger in accordance with the disclosure.
Figure 6B:
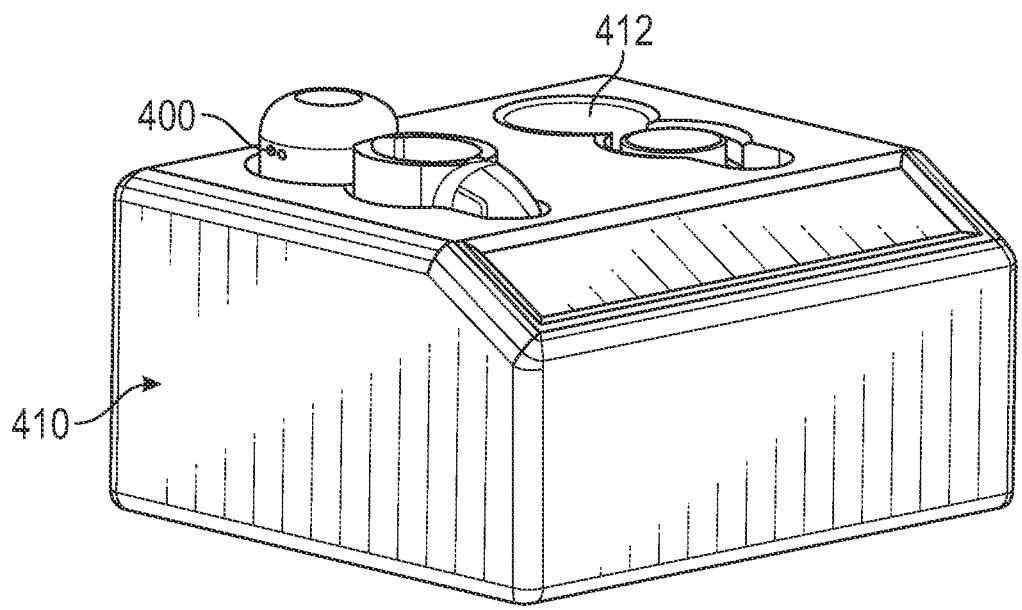
FIG. 6B is a side perspective view of the charger of FIG. 6A in accordance with the disclosure.

In one aspect of the disclosure, as depicted in FIGS. 6A and 6B the pods 400 are supplied as a pair of pods 400 and include a charger 410 configured to receive the two pods 400. The charger includes two cavities 412 configured to receive a pod 400. The cavity includes an interface for electrically connecting the charger 410 to the pod 400 to charge the battery 404. The charger 410 may also include a data connection, not shown, to enable updates of the firmware and software operating on rechargeable battery or the microcontroller 407 or other components of the pod 400. The charger 410 may optionally include one or more LEDs 418 to provide an indication of the power level of batteries 404 of the pods 400 while they are in the charger 410. The charger may optionally also include a display 420 for displaying information regarding the status of the batteries 404, state of charge, number of recharges before replacement of the pod 400, and other useful information to the user. Either the display 420 or the LEDs (or both) may initiate when the pod 400 is placed in the charger 410. Colored LEDS may indicate battery status.

The charger 410 may be placed in the operating room proximate the system 100 such that should a battery of a pod 400 run low of power during a procedure, the pod 400 may be replaced. The charger 410 may be a wireless charger (e.g., inductive charging) requiring no direct electrical connection between the charger 410 and the battery 404 in the pod 400. In addition to the second pod 400, which can be charging during the procedure where the first pod 400 is being used, the connection of the cable 208 remain available for connection to the hub 202. Accordingly, a clinician can have confidence that they will never be without a means of receiving the data from the sensor 107 on the catheter 106.

The pod 400 is configured to rest comfortably in the hand of the user. In accordance with this aspect, the battery 404 is located on one side of the pod 400 and the opposite side of the pod 400 houses the circuit boards and other aspects related to the BLUETOOTH transmitter or transmitter receiver 406. This arrangement allows the weight of the battery to be counterbalanced by the weight of the transmitter 406 and other electrical components. The pod 400 may automatically power up when removed from the charger 410, lighting one of the LEDs 402, and further LEDs 402 may light when electrically connected to the sensor 107, and to the computer 112 via the BLUETOOTH transmitter 406. A speaker 416 may also be employed to provide audible reminders, for example to remove the pod 400 following a procedure or in combination with the connections described above and the lighting of the LEDs.

Alternatively, the pod 400 may include an EM field detector 417. The EM field detector 417 can detect whenever it is placed in an EM field, such as that generated by the transmitter mat 118. Thus rather than requiring an external on/off switch to turn the pod 400 on or off, whenever the pod 400 is within the EM field, the pod 400 fully powers on. In one embodiment the pod 400 may be powered by the magnetic field. Alternatively, the EM field detector 417 can energize a switch not shown, connecting the battery 404 to the wireless transmitter 406. In either configuration the user can be assured that pod 400 is on and transmitting to the locating module 110 and the computer 112 throughout the procedure so long as the pod 400 is in the EM field.

In a further embodiment, the sensors 107 may effectively be the EM field detector. In such an embodiment, the sensor 107 is in communication with the POD 400, and particularly the microcontroller 407. When the sensor 107 is in the EM field, a current and a voltage are generated and used to determine the location of the sensor 107 in the EM field. The voltage may additionally be applied to the microcontroller 407, and logic stored in or applied by the microcontroller 407 upon receipt of this voltage signal can trigger the battery 404 to fully power the pod 400. Additionally or alternatively, the current induced in the sensor 107 may be applied to the battery 404 to charge the battery 404 while it is in the EM field.

This arrangement allows for continued use of the locatable guide 300 during initial navigation to a target. Further the entanglement issues stemming from having two cables 208 and 306 are eliminated. Further, the wireless transmitter 406 ensures that position and orientation in 5DOF continues to be provided to the locating module 110 and computer 112 from the sensor 107 at the distal end of the catheter 106.

In a further aspect of the disclosure, in addition to the wireless transmitter 406 and the battery 404, there is housed in the pod 400 a gyroscopic sensor 414. The gyroscopic sensor 414 is able to determine the orientation of the pod 400 with respect to roll. Thus, there is a 0 position, and based on that known 0 position as the pod 400 is rotated, a determination can be made of how far removed from the 0 position, angle of roll the pod 400 has experienced.

The catheter 106 is typically formed of several layers of polymeric material sandwiching a braided mesh. During manufacturing, reflowing of the polymeric materials results in the formation of a substantially uniform construction. The catheter 106 is flexible but retains substantial resistance to torsion along its length. As a result, a roll of the pod 400 corresponds to a roll experienced at the distal end of the catheter 106 within some factor (e.g., 5, 10, 15, 20, 25%). Thus, by knowing the amount of roll experienced at the pod 400 the direction of roll of the distal end of the catheter 106 is known and an estimate of the magnitude of the roll can be ascertained.

The display 408 on the pod 400 may present an indicator of the number of degrees relative to a 0 position. For example, a +10 degree indicator could indicate a 10 degree rotation in the clockwise direction, and a −10 degree indicator a 10 degree rotation in the counterclockwise direction.

As will be appreciated, algorithms may be developed to refine the estimate based on a number of factors including rigidity of the catheter to twist, the lubricity of the outer material of the catheter, the general lubricity of the airways of a patient, the number of bends the catheter has experienced to achieve its current position, the magnitude in degrees of the bends the catheter 106 has experienced to achieve its current position, the size of the airway in which the distal end of the catheter 106 is currently located, an observed rate of change of position of the distal end of the catheter 106 while the pod is being rotated, and other factors.

The roll experienced by the pod 400, and the estimate that provides for the roll experienced by the distal end of the catheter 106, when combined with the 5 DOF data provided by the sensor at the distal end of the catheter 106 can be combined to provide 6 DOF sensor information about the sensor 107 and the distal end of the catheter 106 to the locating module 110 and computer 112. Such an arrangement may be used with the locatable guide 300, as described above, and simply provide greater clarity of information after removal of the locatable guide 300 from the catheter 106. For instance, in its simplest form, the data may be used to provide an indicator to the clinician on the display 114 that the catheter 106 has likely experienced a roll greater than a preset amount (e.g., 5 degrees). Alternatively, it may be actively relied upon to provide updated roll information to the locating module 110 and computer 112 such that the position of the catheter 106 in the 3D model displayed on the display 114 is constantly updated much the same way it was when employing the locatable guide 300.

Alternatively, the use of the gyroscopic sensor 414 in the pod 400 may enable elimination of the use of the locatable guide 300 from the procedure entirely. This will result in fewer times that a clinician will have to remove a very long instrument from the catheter 106, and in general ease the workflow of the procedure. In addition, elimination of the locatable guide 300 reduces the number of components necessary for a procedure and thus the overall cost of a procedure, while at the same time promoting efficiency and speeding up the time of the procedure. And because the pod 400 is reusable, the overall number of disposable components is also reduced.

In this aspect of the disclosure, only the catheter 106 need be navigated along the planned pathway to a target. The lumen of the catheter 106 may remain open throughout the navigation phase or a tool such as a biopsy or therapy tool may be present in the lumen through the navigation. The data from the sensor 107 at the end of the catheter 106 is combined with the data from the gyroscopic sensor 414 and transmitted via the transmitter 406 to locating module 110 and computer 112 such that the position of the catheter 106 within the patient can be accurately reflected in the 3D model.

Where fluoroscope 116 is employed, the clinician may navigate the bronchoscope 104 and catheter 106 proximate a target. Once proximate the target, a fluoroscopic sweep of images may be acquired. This sweep is a series of images (e.g., video) acquired for example from about 15-30 degrees left of the AP position to about 15-30 degrees right of the AP position. Once acquired, the clinician may be required to mark one or more of the bronchoscope 104, catheter 106, or target 308 in one or more images. Alternatively, image processing techniques may also be used to automatically identify the bronchoscope 104, catheter 106, or target 308.

For example, an application running on computer 112 may be employed to identify pixels in the images having relevant Hounsfield units that signify the density of the bronchoscope 104 and catheter 106. The last pixels before a transition to a less dense material may be identified as the distal locations of the bronchoscope 104 and catheter 106. This may require a determination that the pixels having the Hounsfield unit value indicating a high-density material extent in a longitudinal direction at least some predetermined length. In some instances, the target may also be identified based on its difference in Hounsfield unit value as compared to surrounding tissue. With the bronchoscope 104 and catheter 106 positively identified, a 3D volumetric reconstruction of the luminal network can be generated. The 3D volumetric construction may then be analyzed using similar image processing techniques to identify those pixels in the image having a Hounsfield unit signifying the density of the airway wall. Alternatively, the imaging processing may seek those pixels having a Hounsfield unit signifying air. In this process, all of the pixels having a density of air are identified until a change in density is detected. By performing this throughout the 3D volumetric construction, the relative position and orientation of the target and the catheter 106 can be determined and used to update their depicted positions in the 3D model on computer 112.

Figure 7A:
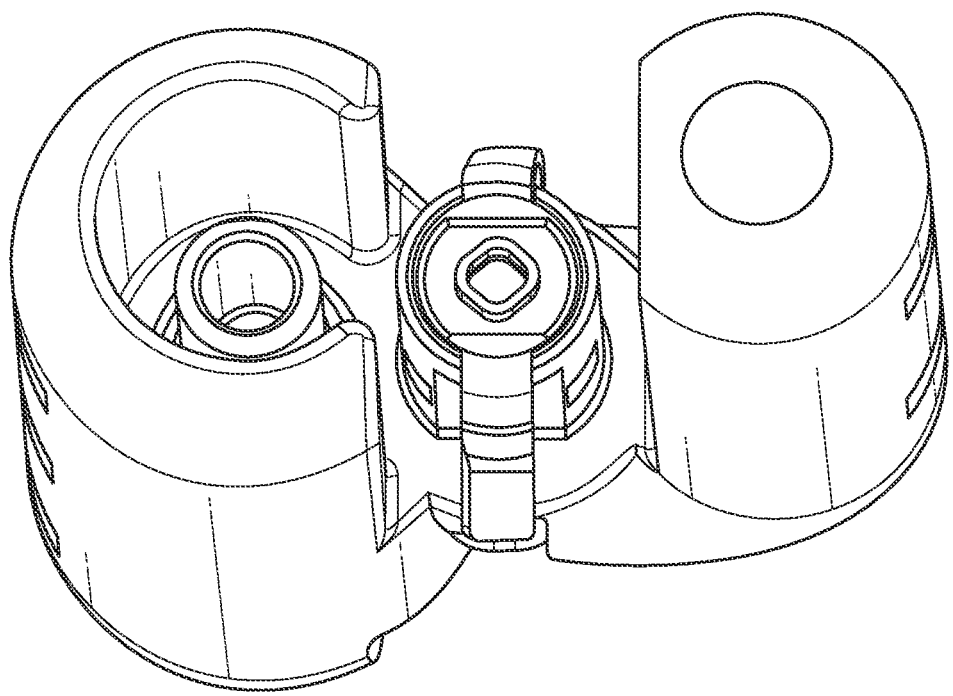
FIG. 7A is an end view of the wireless transmission pod of FIG. 5.
Figure 7B:
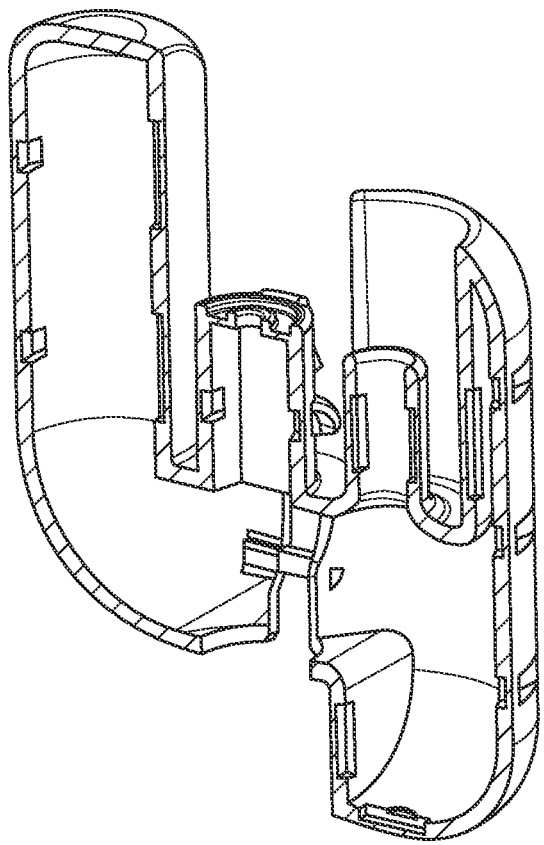
FIG. 7B is a cross-sectional view of the wireless transmission pod of FIG. 5.
Figure 8A:
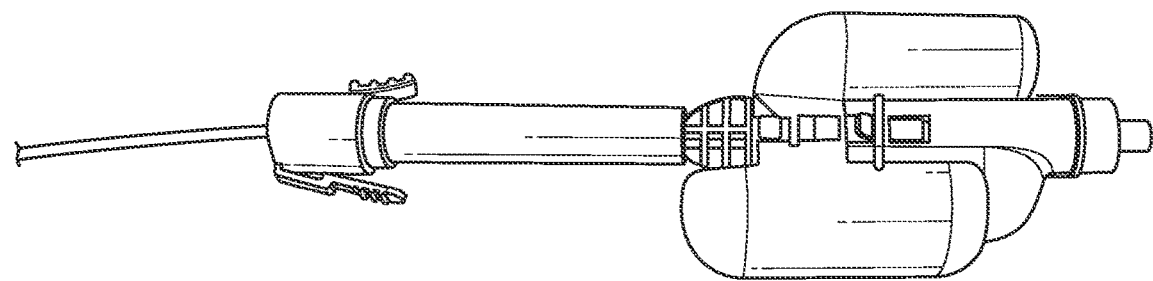
FIG. 8A is a comparative view of the wireless transmission pod incorporated as part of a catheter of FIG. 4 and the wireless transmission pod of FIG. 5.
Figure 8A:
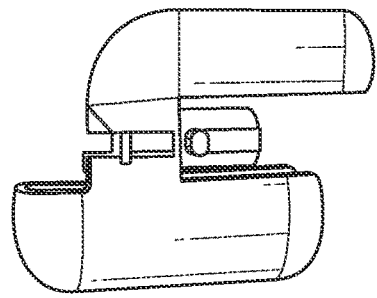
Figure 8B:
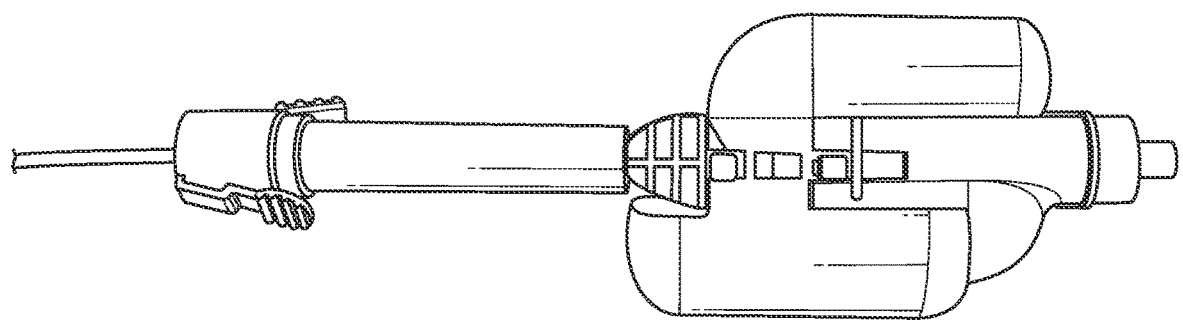
FIG. 8B depicts the wireless transmission pod incorporated as part of a catheter being held by a user.

FIG. 7A depicts a top end view of the wireless transmission pod 400 and FIG. 7B depicts a cross sectional view of the wireless transmission pod. FIG. 8A depicts a comparative view of the wireless transmission pod 400 incorporating the catheter 106 and hub 200. FIG. 8B shows the wireless transmission pod 400, hub 200, and catheter 106 in the hand of the user as it might be used during a procedure.

Figure 9A:
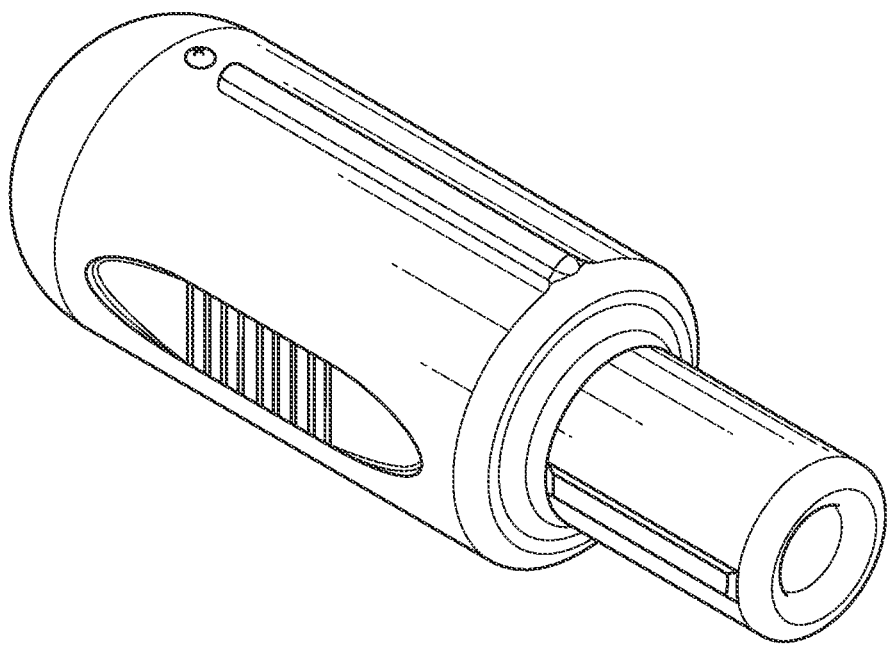
FIGS. 9A-9E depict an alternative form of a wireless transmission pod and its incorporation into a catheter in accordance with the disclosure.
Figure 9B:
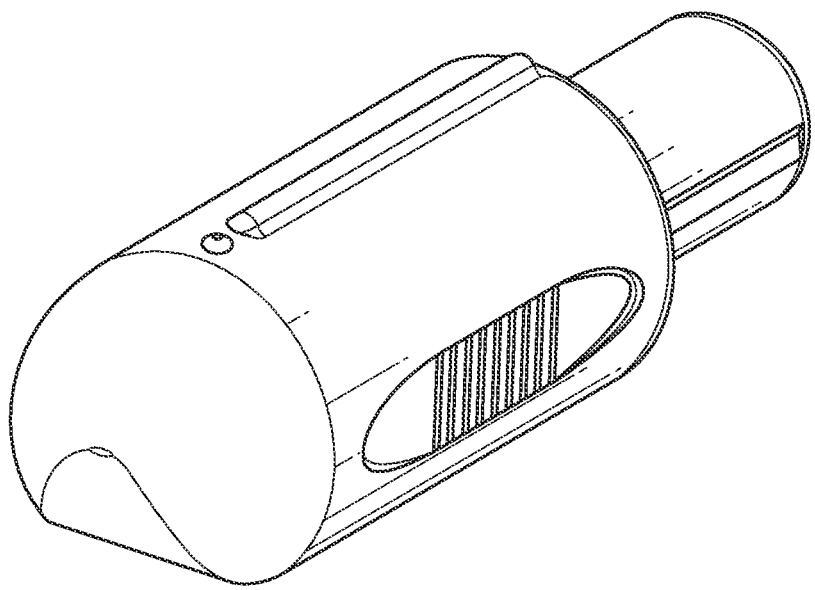
Figure 9E:
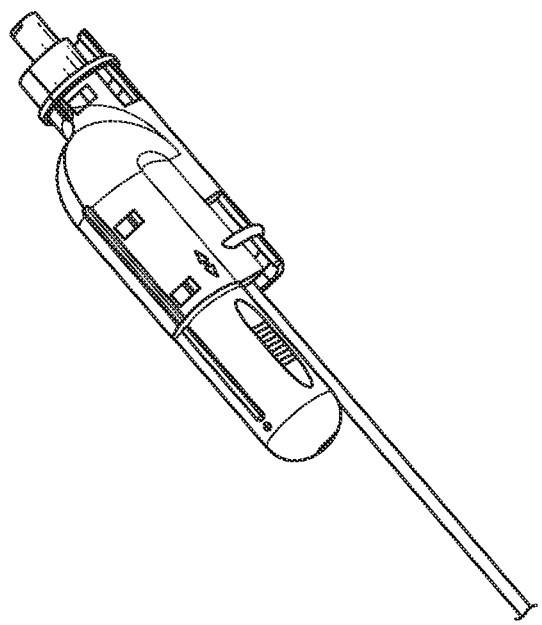
Figure 9D:
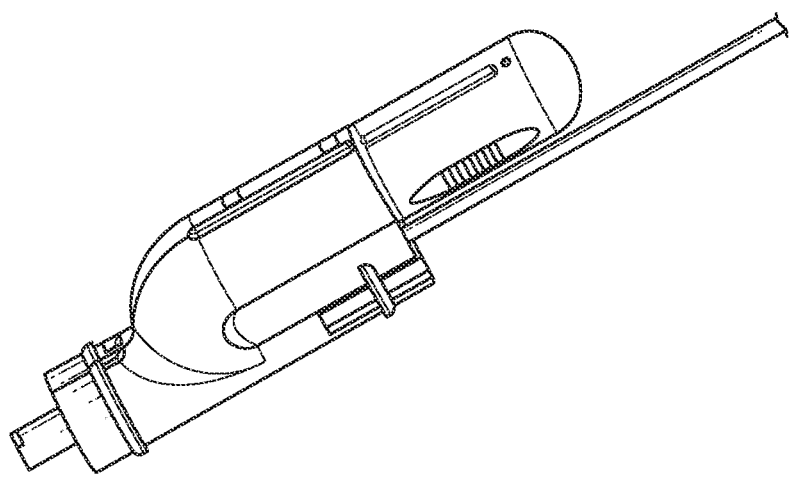
Figure 9C:
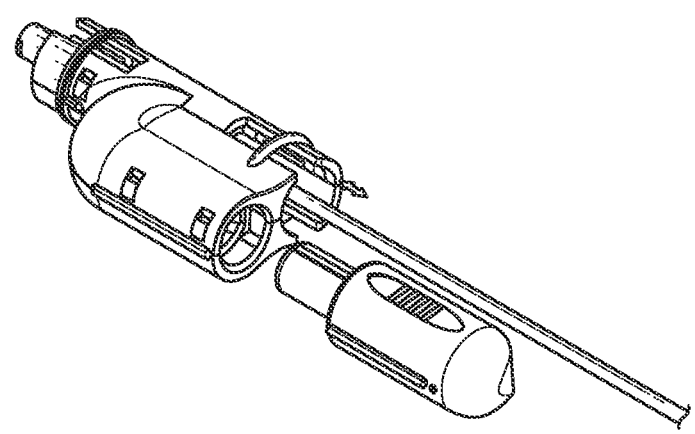
Figure 10A:
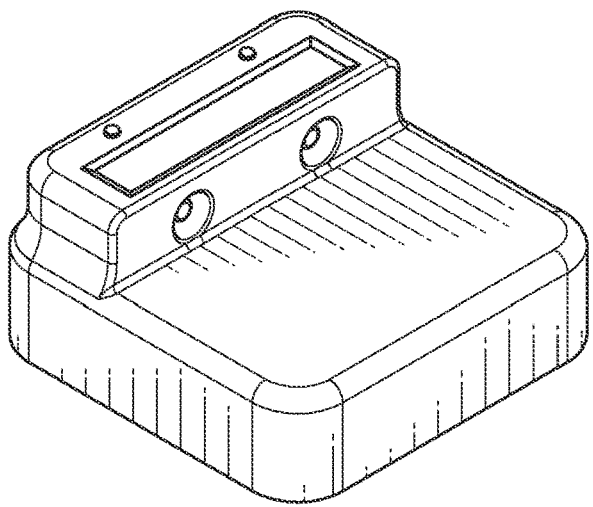
FIGS. 10A-10C depict a charger for use with the wireless transmission pods of FIG. 9A.
Figure 10B:
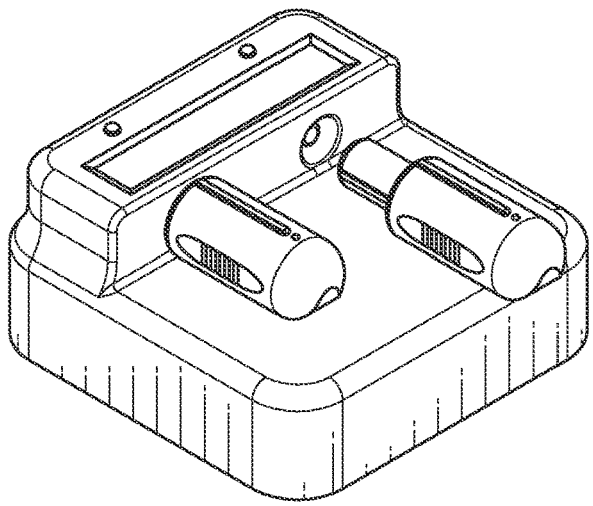
Figure 10C:
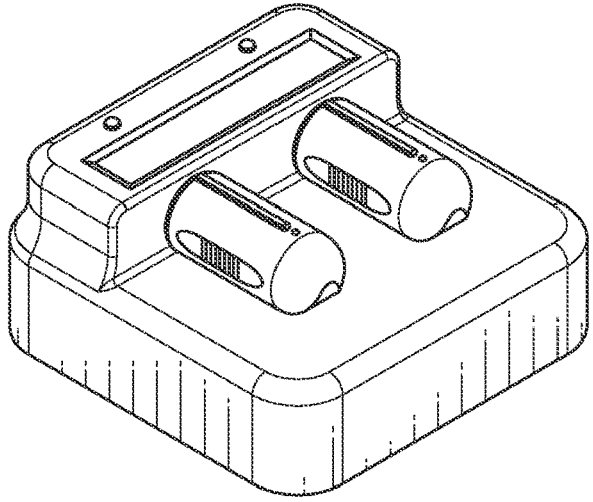

While the foregoing has described specific functionality of the wireless transmission pod 400 and its incorporation with the catheter 106. FIGS. 9A and 9B depict an alternative form of the wireless transmission pod 400. FIGS. 9C-9E depict various views of insertion of the wireless pod 400 of inserted into the hub 200 with catheter 106. FIGS. 10A-C depict a charger for receiving and recharging the internal battery of the wireless transmission pod 400 of FIGS. 9A and 9B.

Figure 5:
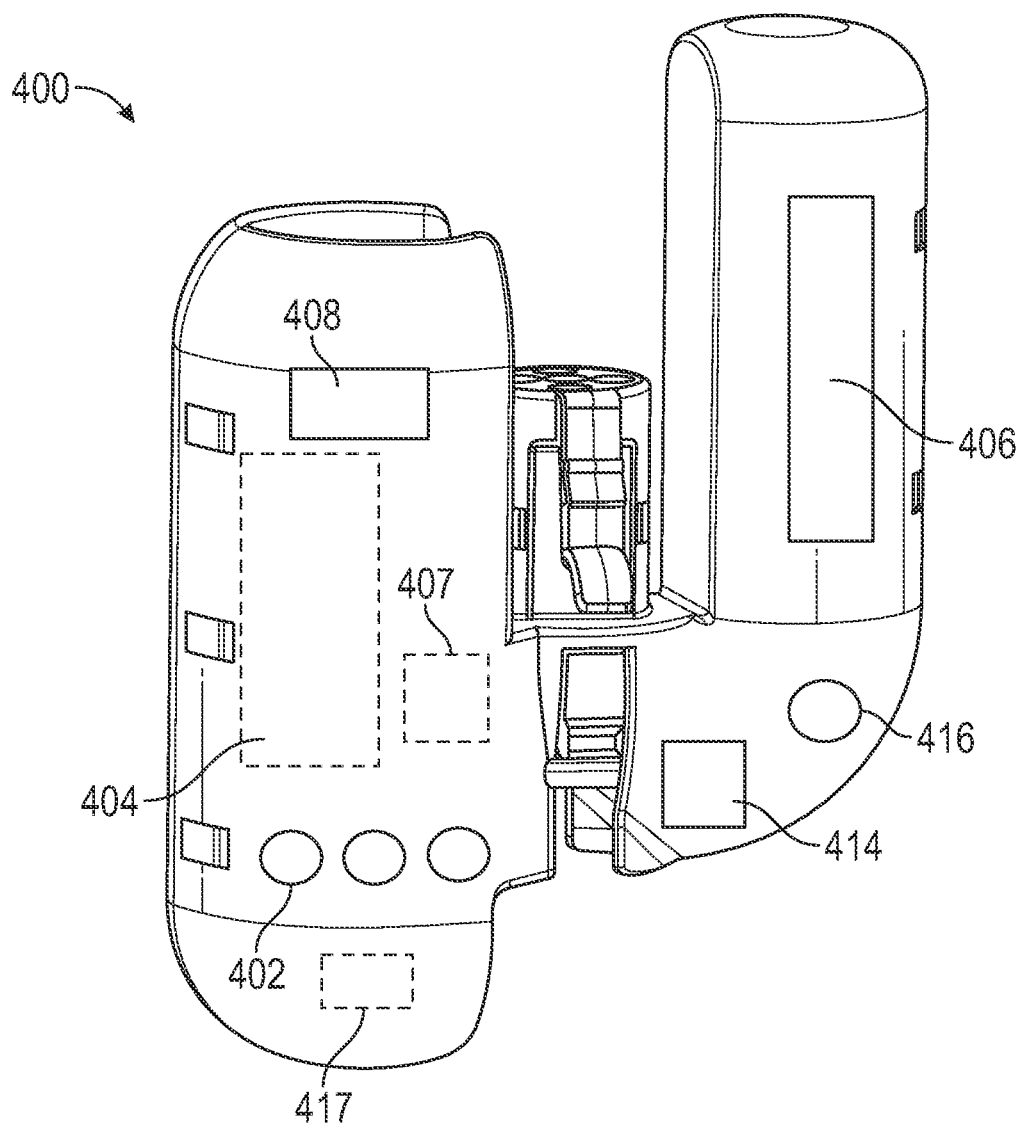
FIG. 5 is a perspective view of a wireless transmission pod.
Figure 11A:
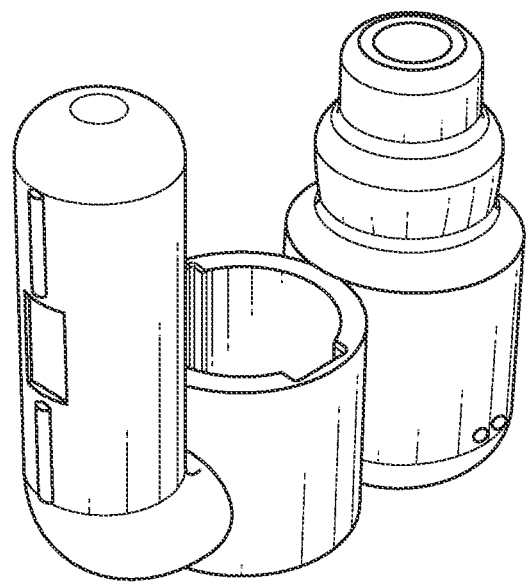
FIGS. 11A-11E depict an alternative form of a wireless transmission pod and its incorporation into a catheter in accordance with the disclosure.
Figure 11B:
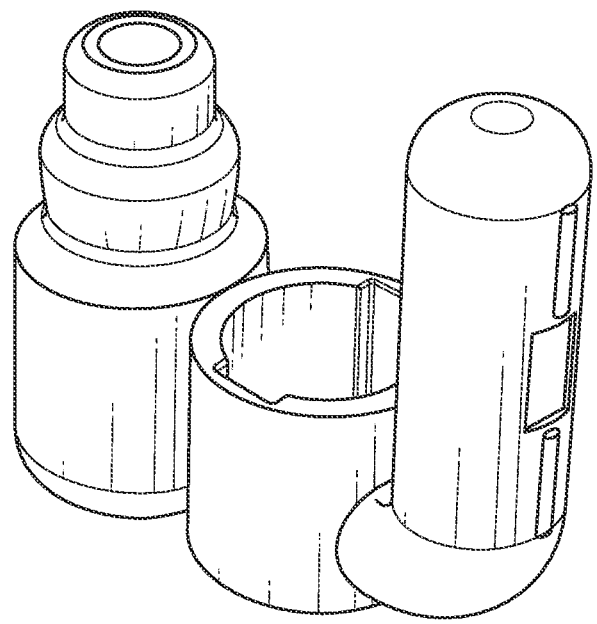
Figure 11C:
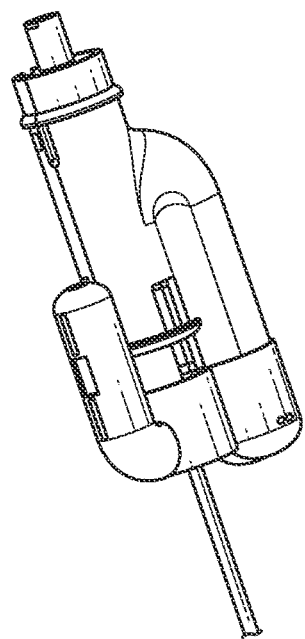
Figure 11D:
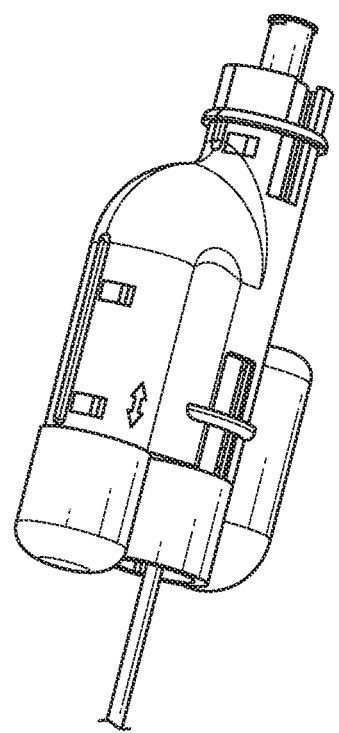
Figure 11E:
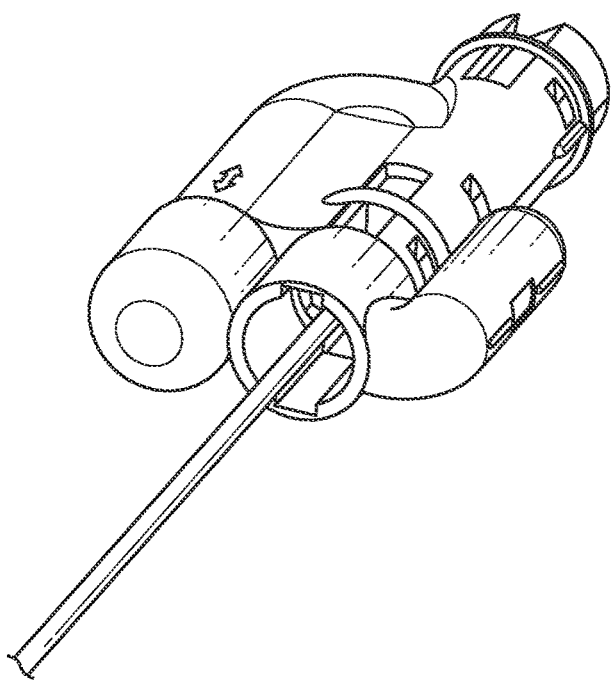
Figure 12B:
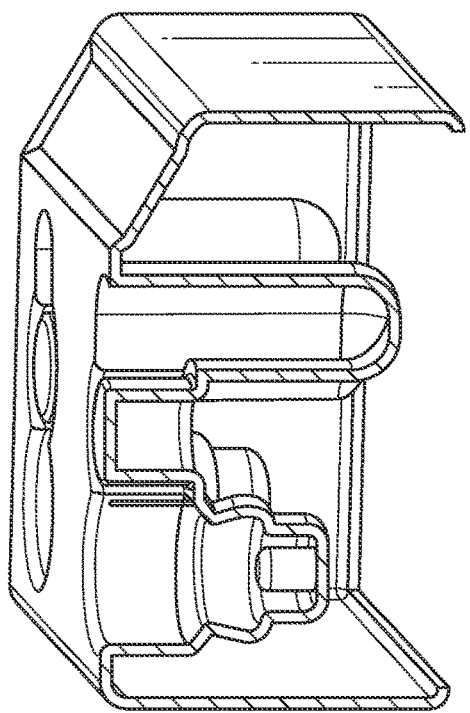
FIGS. 12A-12D depict a charger for use with the wireless transmission pods of FIG. 11A.
Figure 12D:
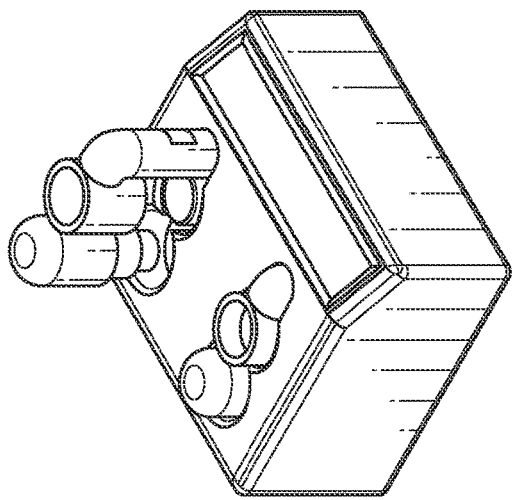
Figure 12A:
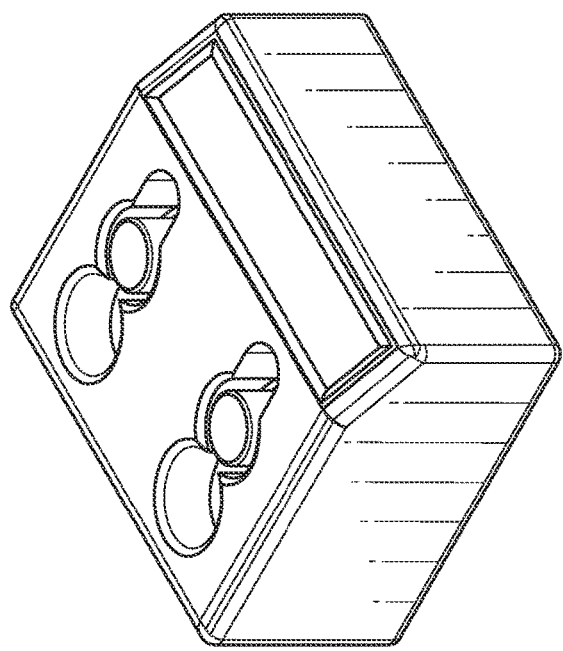
Figure 12C:
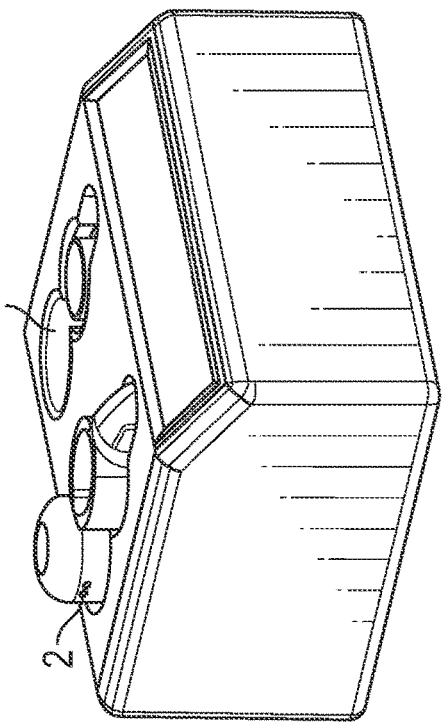

FIGS. 11A and 11B depict another alternative form of the wireless transmission pod 400. The version in FIGS. 11A and 11B are similar in form to that depicted in FIG. 5. FIGS. 11C-11E depict various views of insertion of the wireless pod 400 of inserted into the hub 200 with catheter 106. FIGS. 12A-D depict a charger for receiving and recharging the internal battery of the wireless transmission pod 400 of FIGS. 11A and 11B.

Figure 13A:
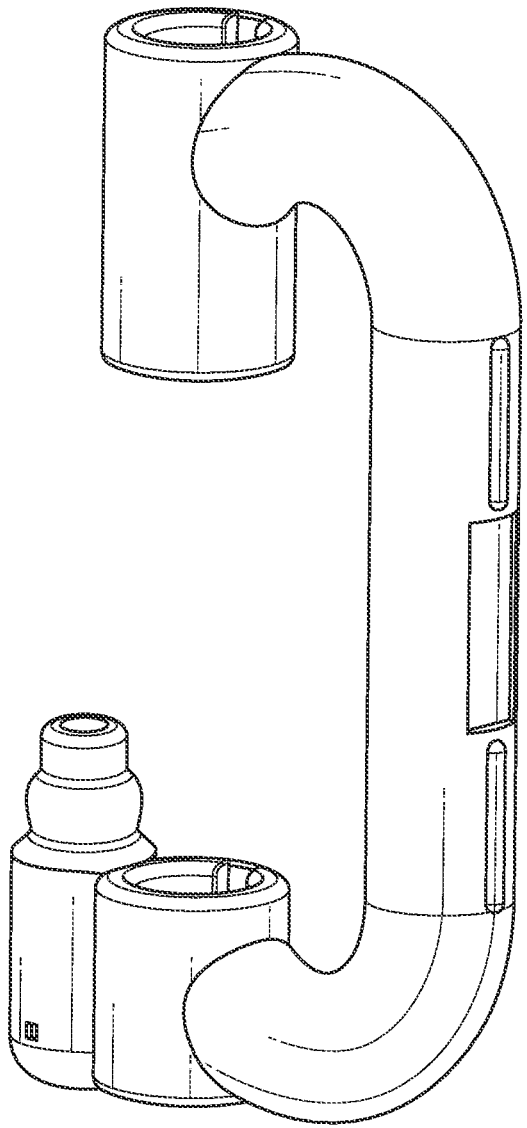
FIGS. 13A and 13B depict an alternative form of a wireless transmission pod and its incorporation into a catheter in accordance with the disclosure.
Figure 13B:
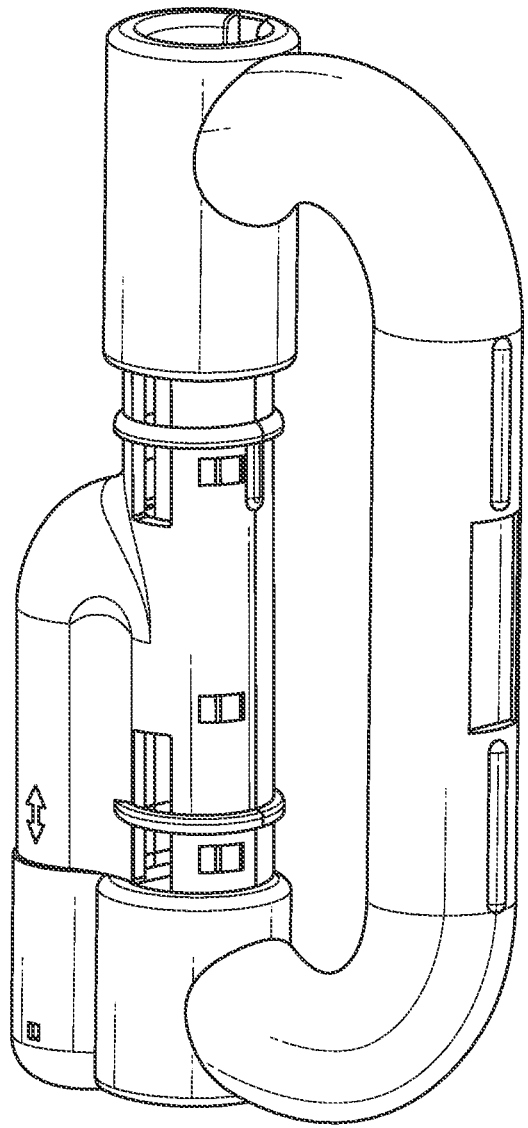
Figure 14A:
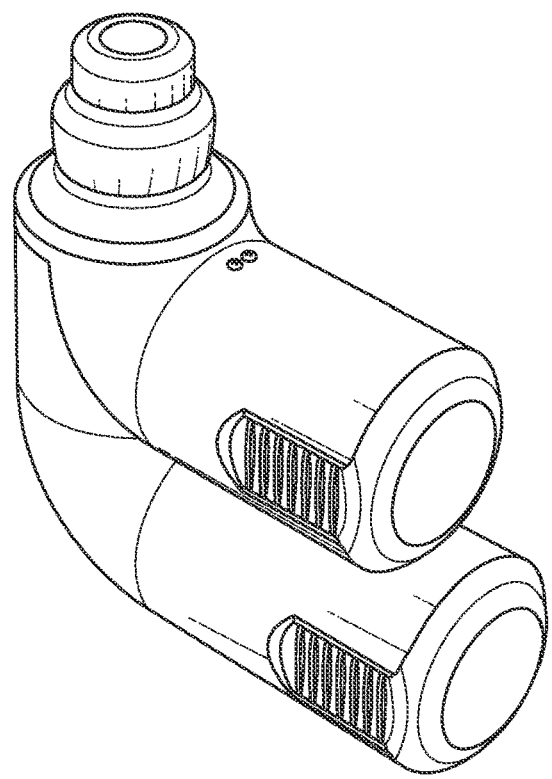
FIGS. 14A-14E depict an alternative form of a wireless transmission pod and its incorporation into a catheter in accordance with the disclosure.
Figure 14B:
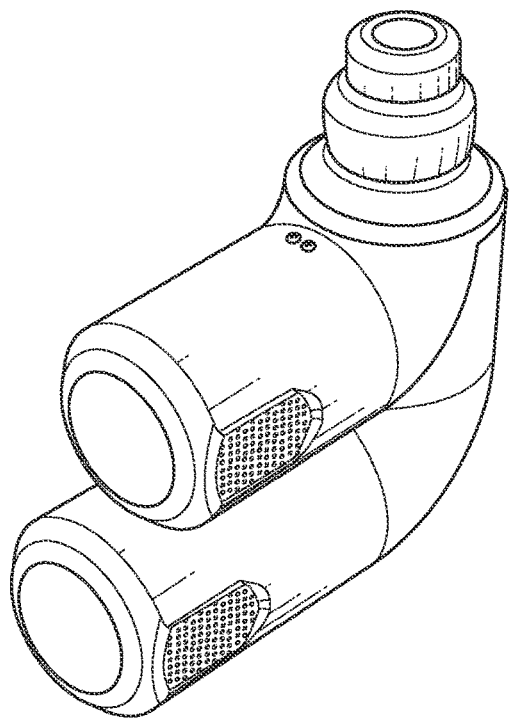
Figure 14C:
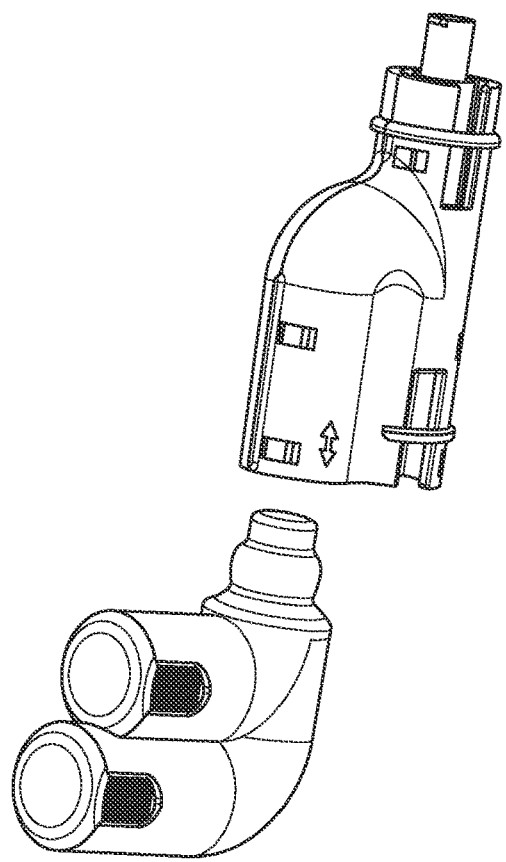
Figure 14D:
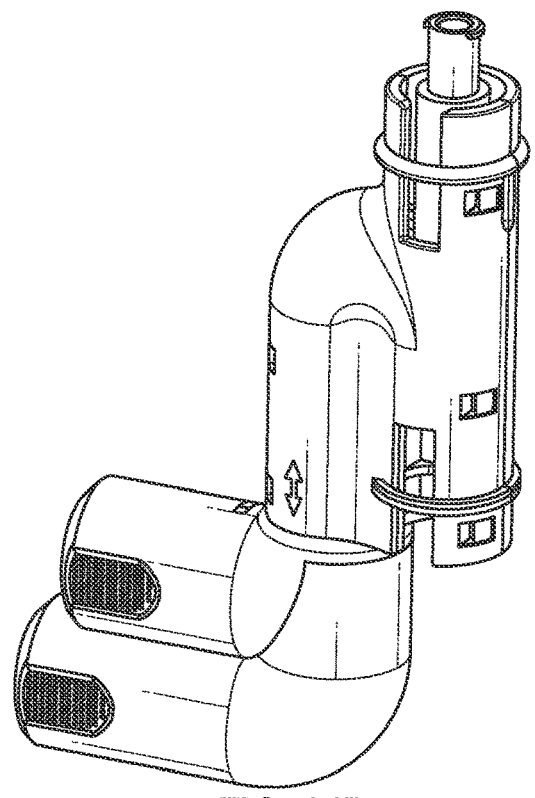
Figure 14E:
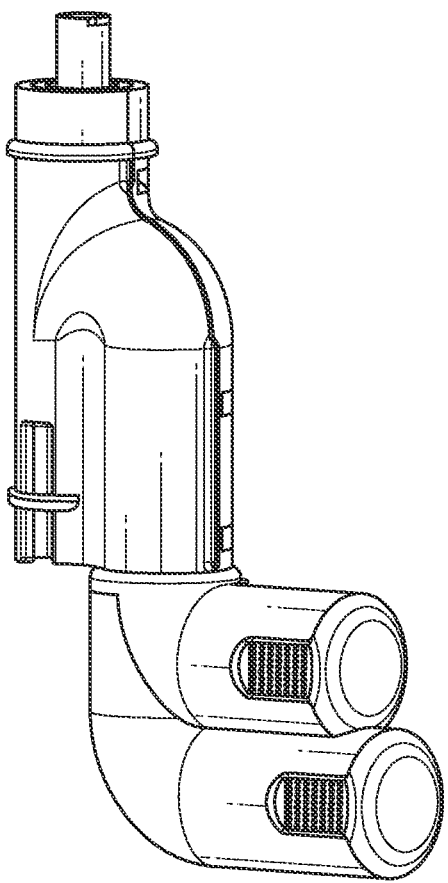
Figure 15A:
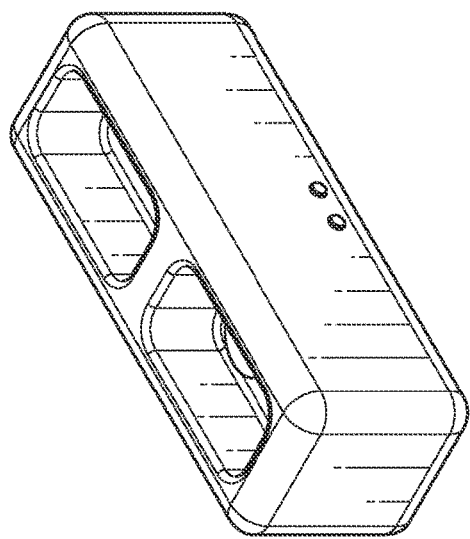
FIGS. 15A-15D depict a charger for use with the wireless transmission pods of FIG. 14A.
Figure 15B:
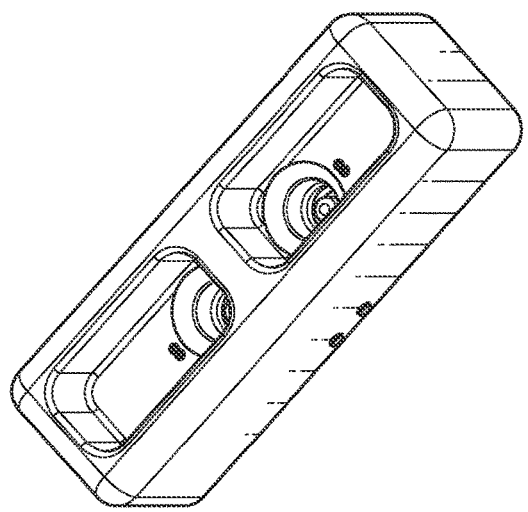
Figure 15C:
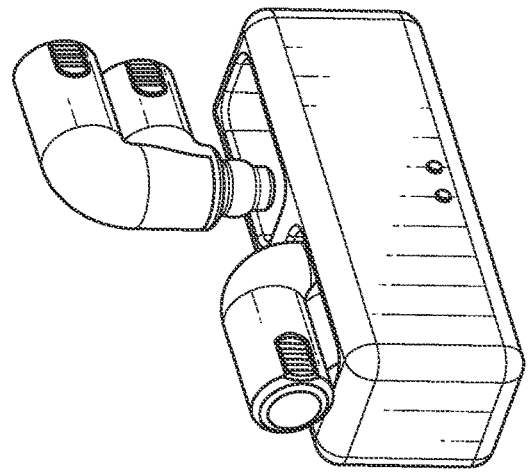
Figure 15D:
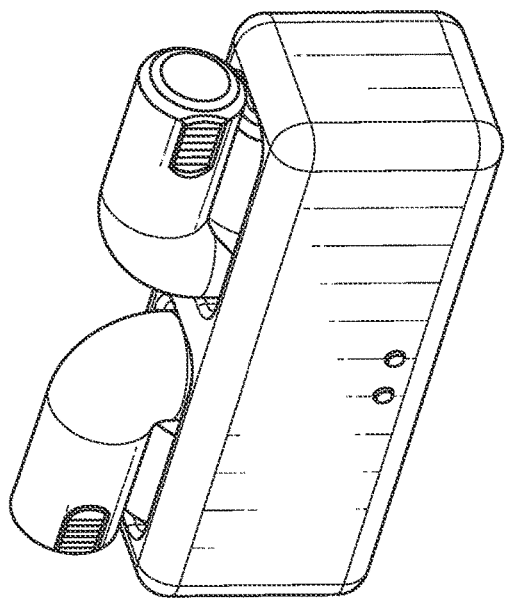

FIGS. 13A and 13B depict another alternative form of the wireless transmission pod 400. As shown in FIG. 13B the wireless transmission pod 400 receives the hub 200 and also provides for a convenient handle for grasping the assembly. FIGS. 14A and 14B depict another alternative form of the wireless transmission pod 400. FIGS. 14C-14E depict various views of insertion of the wireless pod 400 of inserted into the hub 200. FIGS. 15A-D depict a charger for receiving and recharging the internal battery of the wireless transmission pod 400 of FIGS. 14A and 14B.

Throughout this description, the term "proximal" refers to the portion of the device or component thereof that is closer to the clinician and the term "distal" refers to the portion of the device or component thereof that is farther from the clinician. Additionally, in the drawings and in the description above, terms such as front, rear, upper, lower, top, bottom, and similar directional terms are used simply for convenience of description and are not intended to limit the disclosure. In the description hereinabove, well-known functions or constructions are not described in detail to avoid obscuring the disclosure in unnecessary detail.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

What is claimed is:

1. A luminal navigation system comprising:
   a catheter configured for insertion into a bronchoscope, the catheter including a five degree of freedom (5DOF) sensor at a distal portion of the catheter;
   a locating module configured to receive signals from the 5DOF sensor to determine an X, Y, Z location and pitch and yaw orientation of the distal portion of the catheter;
   a pod, including a housing and configured to be received between a telescoping portion of the catheter and a hub of the catheter, the pod including a wireless communication device and an electromagnetic (EM) field detector, wherein the pod powers on upon detection of a magnetic field; and
   a gyroscopic sensor located in the pod, wherein the gyroscopic sensor determines an amount of roll experienced by the pod, wherein the pod is configured to receive signals from the 5DOF sensor and the gyroscopic sensor and to transmit to the locating module the received signals, wherein the locating module determines the position and orientation of the distal portion of the catheter in six degrees of freedom (6DOF).

2. The luminal navigation system of claim 1 further comprising a locatable guide configured for insertion into a lumen of the catheter, the locatable guide including a 6DOF sensor at a distal end and a handle on a proximal end, wherein signals generated by the 6DOF sensor are transmitted to the locating module.

3. The luminal navigation system of claim 2, wherein the 6DOF sensor and the 5DOF sensor are electromagnetic sensors configured to detect magnetic fields generated by a magnetic field generator.

4. The luminal navigation system of claim 1, wherein the pod further includes a rechargeable battery.

5. The luminal navigation system of claim 4, further comprising a charger configured to receive the pod and to charge the rechargeable battery.

6. The luminal navigation system of claim 5, wherein the charger is configured for wireless charging of the rechargeable battery in the pod.

7. A luminal navigation system comprising:
   a catheter configured for insertion into a bronchoscope, the catheter including a five degree of freedom (5DOF) sensor at a distal portion of the catheter;
   a locating module configured to receive signals from the 5DOF sensor to determine an X, Y, Z location and pitch and yaw orientation of the distal portion of the catheter;
   a locatable guide configured for insertion into a lumen of the catheter, the locatable guide including a 6DOF sensor at a distal end and a handle on a proximal end, wherein signals generated by the 6DOF sensor are transmitted to the locating module; and
   a pod, including a housing and configured to be received between a telescoping portion of the catheter and a hub of the catheter, the pod including a wireless communication device; wherein the locating module receives the output from the 6DOF sensor via a cable while the locatable guide is secured in the catheter and the locating module is further configured to receive the output from the 5DOF sensor via the wireless communication device following removal of the locatable guide from the catheter.

8. The luminal navigation system of claim 7, further comprising a gyroscopic sensor located in the pod, wherein the gyroscopic sensor determines an amount of roll experienced by the pod.

9. The luminal navigation system of claim 8, wherein the pod is configured to receive signals from the 5DOF sensor and the gyroscopic sensor and to transmit to the locating module the received signals and the locating module can determine the position and orientation of the distal portion of the catheter in six degrees of freedom (6DOF).

10. The luminal navigation system of claim 7, wherein the pod includes an EM field detector, wherein the pod fully powers on upon detection of a magnetic field.

11. The luminal navigation system of claim 7, wherein the 6DOF sensor and the 5DOF sensor are electromagnetic sensors configured to detect magnetic fields generated by a magnetic field generator.

12. The luminal navigation system of claim 7, wherein the pod further includes a rechargeable battery.

13. The luminal navigation system of claim 12, further comprising a charger configured to receive the pod and to charge the rechargeable battery.

14. The luminal navigation system of claim 13, wherein the charger is configured for wireless charging of the rechargeable battery in the pod.

15. A wireless communication pod for a luminal navigation catheter, comprising:

a housing configured to mate with a catheter, the catheter including a five degrees of freedom (5DOF) sensor formed on a distal end;

a rechargeable battery secured within the housing;

a wireless communication device secured within the housing;

a gyroscopic sensor secured within the housing, an electromagnetic field detector configured to detect an electromagnetic field, and enable the wireless communication device to transmit a signal when an electromagnetic field is detected;

a microcontroller configured to receive signals from the 5DOF sensor and the gyroscopic sensor and to output via the wireless communication device a signal from which a position and orientation of distal portion of the catheter in six degrees of freedom (6DOF).

16. The wireless transmitter pod of claim 15, further comprising at least one light-emitting diode configured to indicate a status of the rechargeable battery.

17. The wireless transmitter pod of claim 15, further comprising at least one light emitting diode configured to indicate a connection status of the wireless communication device.

18. The wireless transmitter pod of claim 15, further configured to receive a hub of the catheter, wherein the hub enables electrical connectivity of the sensor to the microcontroller.

19. The wireless transmitter pod of claim 15, wherein the 5 DOF sensor is an electromagnetic sensor.

* * * * *